United States Patent
Haley et al.

(10) Patent No.: US 7,365,042 B2
(45) Date of Patent: Apr. 29, 2008

(54) PYRIDINE-3-SULFONYL COMPOUNDS AS PESTICIDAL AGENTS

(75) Inventors: Gregory J. Haley, La Jolla, CA (US); Deborah Culbertson, Fuguay-Varina, NC (US); Michael F. Treacy, Newton, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 513 days.

(21) Appl. No.: 10/495,929

(22) PCT Filed: Nov. 22, 2002
(Under 37 CFR 1.47)

(86) PCT No.: PCT/EP02/31368

§ 371 (c)(1),
(2), (4) Date: Aug. 17, 2004

(87) PCT Pub. No.: WO03/043990

PCT Pub. Date: May 30, 2003

(65) Prior Publication Data

US 2006/0167264 A1    Jul. 27, 2006

(51) Int. Cl.
C07D 213/71    (2006.01)
A61K 43/40     (2006.01)

(52) U.S. Cl. ............ 504/130; 546/294; 546/295; 514/347

(58) Field of Classification Search ........ 546/294, 546/295; 514/347; 504/130
See application file for complete search history.

(56) References Cited

U.S. PATENT DOCUMENTS 3,202,576 A    8/1965  Rogers et al.
5,858,924 A  * 1/1999  Johnson et al. ............ 504/241

FOREIGN PATENT DOCUMENTS

EP        356 029       2/1990

OTHER PUBLICATIONS

Synthesis, Nov. 1996, XP-001145425, 13751379, Fanghaenel et al.

* cited by examiner

Primary Examiner—Zinna N. Davis
(74) Attorney, Agent, or Firm—Novak Druce + Quigg LLP

(57) ABSTRACT

The present invention describes novel pyridine-3-sulfonyl compounds having the formula (I)

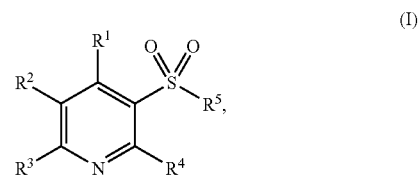

(I)

wherein $R^1$, $R^2$, $R^3$, $R^4$ and $R^5$ are as defined herein.

The present invention is also directed lo pesticidal compositions that include a) compounds of formula (II)

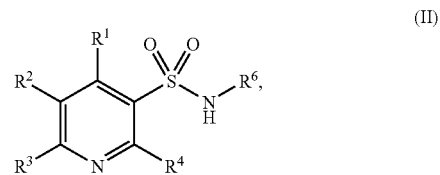

(II)

wherein $R^1$, $R^2$, $R^3$, $R^4$ and $R^6$ are as defined herein and b) a carrier.

Moreover, the present invention relates to methods for protecting crops from insect attack by contacting the crop with a pesticidally effective amount of the compound of formula (II). In addition, the present invention includes methods for controlling insects by treating the target species with a pesticidally effective amount of the compound of formula (II).

17 Claims, No Drawings

PYRIDINE-3-SULFONYL COMPOUNDS AS PESTICIDAL AGENTS

The present invention relates to pesticidal compounds and their methods of use as pesticidal agents. In particular, the present invention relates to pyridine-3-sulfonyl compounds, compositions and method of their use as pesticides.

In spite of the commercial pesticides available today, damage to crops, both growing and harvested, caused by insects and nematodes still occurs. For example, aphids are pests of vegetables, field crops, and fruit trees, as well as nearly all indoor and outdoor ornamental plants. Similarly, mites may cause yield losses by themselves or they may join with other soil borne organisms such as viruses, fungi and bacteria, to promote disease development in plants. As such, there is continuing need to develop new and more effective pesticidal agents. The present invention has found that certain pyridine-3-sulfonyl compounds have useful pesticidal properties.

As embodied and broadly described herein, the present invention, in one aspect, relates to compounds of formula (I)

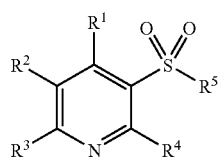
(I)

and the isomers, salts and esters thereof, wherein the substituents are described further in the detailed description.

In addition, the present invention includes compounds of formula (II)

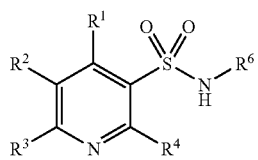
(II)

and the isomers, salts and esters thereof, wherein the substituents are described further in the detailed description.

Moreover, the compounds of formula (II) may be included in compositions that include, in addition to the compound, an agronomically acceptable carrier.

In another embodiment, the present invention relates to a method for the control of insects or nematodes by contacting an insect or nematode or their food supply, habitat or breeding grounds with a pesticidally effective amount of a compound of formula (II).

Furthermore, the present invention also relates to a method of protecting growing plants from attack or infestation by insects or nematodes by applying to the foliage of the plants, or to the soil or water in which they are growing, a pesticidally effective amount of a compound of formula (II).

Advantages of the invention will be set forth in part in the description which follows, and in part will be obvious to those skilled in the art from the description, or may be learned by practice of the invention. It is to be understood that both the foregoing general description and the following detailed description are exemplary and explanatory only and are not restrictive of the invention, as claimed.

The present invention may be understood more readily by reference to the following detailed description of exemplary embodiments of the invention and the examples included therein.

Before the present compounds, compositions, and methods are disclosed and described, it is to be understood that this invention is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

The term "alkenyl" as used herein intends a branched, unbranched, or cyclic unsaturated hydrocarbon group containing at least one double bond. One or more hydrogen atoms of the alkenyl group may be replaced with one or more functional groups an any position of the alkenyl group $C_2$-$C_4$-alkenyl includes, without limitation, ethenyl, 1-propenyl, 2-propenyl, 1-butenyl, 2-butenyl, 3-butenyl, and the like. Geometric structures such as (AB)C=C(CD) are intended to include all isomers.

The term "alkyl" as used herein refers to a branched, unbranched, or cyclic saturated hydrocar-bon group. One or more hydrogen atoms of the alkyl group may be replaced with one or more functional groups on any position of the alkyl group. Specifically, $C_1$-$C_4$-alkyl includes, without limitation, methyl, ethyl, n-propyl, isopropyl, n-butyl, isobutyl, t-butyl and the like.

The term "alkynyl" as used herein refers to a branched, unbranched, or cyclic unsaturated hy-drocarbon group containing at least one triple bond. One or more hydrogen atoms of the alkynyl group may be replaced with one or more functional groups an any position of the alkynyl group. In particular, $C_2$-$C_4$-alkynyl includes ethynyl, 1-propynyl, 2-propynyl, 1-butenyl, 2-butenyl, 3-butenyl, and the like. Geometric structures such as (AB)C≡C(CD) are intended to include all isomers.

One or more hydrogen atoms of the phenyl group may be replaced with one or more functional groups. Such substituents may be present an any position, i.e. ortho, meta or para positions.

"Halogen" will be taken to mean fluoro, chloro, bromo and iodo.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. One of ordinary skill in the art will recognize that the potency and, therefore, a "pesticidally effective amount" can vary for the various compounds/compositions used in the invention.

"Locus" means a plant, seed, soil, area, material or environment in which an insect is growing or may grow. Exemplary plants and seeds include crop plants and their seeds or nuts, such as vines, wheat, barley, apples, tomatoes, rye, soybeans, oats, rice, maize, lawn, bananas, cotton, coffee, sugar cane, grapevines, fruit species, ornamentals, cucumbers, beans, tomatoes, potatoes and cucurbits.

By "mites" is meant herbivorous mites, including but not limited to, *Tetranychidae* spp. such as *Tetranychus urticae*, *Tetranychus pacificus*, *Tetranychus kanzawai*, *Panonychus ulmi*, *Panonychus citri* and *oligonychus pratensis*; *Tarson-*

*emidae* spp. such as *Phytonemus pallidus* and *Polyphagotarsonemus latus*; *Eriophyidae* spp. such as *Aculus schlechtendali*, *Phyllocop-trataoleivora* and *Eriophyes sheldoni*; and *Tenuipalpidae* spp. such as *Brevipalpus phoenicis*. In particular, the compounds of this invention are especially useful for the control of *Tetranychus urticae, Panonychus ulmi, Panonychus citri* and *Brevipalpus phoenicis*.

As used herein, "insects" include a variety of insects including, but not limited to mites, *Lepidoptera* such as tobacco budworms, cabbage loopers, cotton boll worms, beet armyworms, southern annyworms and diamondback moths; *Coleoptera* such as boll weevils, Colo-rado potato beetles, southern corn rootworms, western corn rootworms and mustard beetles; *Homoptera* such as leaf hoppers, plant hoppers, white flies, and aphids including, but not limited to soft-fruit aphids such as *A. forbesi, A. grossulariae, A. schneideri, Chaetosiphon fragaefolii, Cryptomyzus ribis*, and *Hyperomyzus lactucae*; pomaceous aphids such as *A. pomi, Dysaphis plantaginea, D. pyri, Melanaphis pyrarius* and *Rhopalosiphum insertum*; plum aphids such as *Brachycaudus helichrysi, B. persicae, B. prunicola, Hyalopterus pruni, Myzus cerasi, M. persi-cae, M. varians, Phorodon humuli*; citrus aphids such as *Aphis spiraecola* and *Toxoptera auran-tii*; cereal aphids such as *Metopolophium dirhodum, Rhopalosiphum padi* and *Sitobion avenae*; pests of other field crops such as *Acyrthosiphon pisum, Aphis gossypii, Aphis fabae, Aula-corthum solani, Brachycaudus cardui, Brevicoryne brassicae, Capitophorus horni, Macrosiphum euphorbiae, Myzus ascalonicus*, and *Nasonovia ribis-nigri*.

"Salt" as used herein those compounds that can form with, for exanlple, amines, metals, alkaline earth metal bases or quaternary ammonium bases, including zwitterions. Suitable metal and alkaline earth metal hydroxides as salt formers include the salts of barium, aluminum, nickel, copper, manganese, cobalt zinc, fron, silver, lithium, sodium, potassium, magnesium or calcium. Additional salt formers include chloride, sulfate, acetate, carbonate, hydride, and hydroxide. Desirable salts include maleic acid, dimaleic acid and methane sulfonic acid.

As used throughout, the phrase, "contacting" is used to mean that the insect, plant and/or soil or water in which the plant is growing has contact with the present compound(s) or composition(s) by any application method known in the art. As such, "contacting" includes both direct contact (applying the compound/composition directly an the insect and/or plant) and indirect contact (applying the compound/composition to the locus of the insect, and/or plant).

The pesticidal compositions of the present invention include compounds having the formula (I)

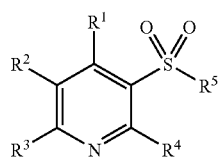

(I)

wherein
$R^1$ is nitro, $C_1$-$C_4$-alkyl, $C_2$-$C_4$-alkenyl, $C_2$-$C_4$-akynyl or phenyl, wherein the alkyl, alkenyl, alkynyl and phenyl groups may be substituted with at least one halogen or at least one cyano;

$R^2$, $R^3$ and $R^4$ are each independently hydrogen, nitro, $C_1$-$C_4$-alkyl, $C_2$-$C_4$-alkenyl, $C_2$-$C_4$-akynyl or phenyl, wherein the alkyl, alkenyl, alkynyl and phenyl groups may be substituted with at least one halogen or at least one cyano;

$R^5$ is halogen or NH—$R^6$;

$R^6$ is $C_1$-$C_4$-alkyl, $C_2$-$C_4$-alkenyl, $C_2$-$C_4$-alkynyl or phenyl, wherein the alkyl, alkenyl, alkynyl and phenyl groups may be substituted with at least one halogen or at least one cyano;

or the isomers, salts or esters thereof.

In one embodiment, $R^5$ is halogen. In another embodiment, $R^1$ is trifluoromethyl and $R^5$ is halogen. In yet another embodiment, compounds of formula (I) include 4-trifluoromethylpyridine-3-sulfonyl chloride.

In a further embodiment, $R^5$ is NH—$R^6$, such as shown in formula (II)

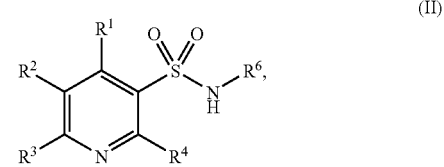

(II)

wherein $R^1$, $R^2$, $R^3$, $R^4$ and $R^6$ are as defined for formula (I).

In still a further embodiment, $R^1$ is trifluoromethyl and $R^5$ is NH—$R^6$. In yet another embodiment, $R^1$ is trifluoromethyl; $R^2$, $R^3$ and $R^4$ are each independently hydrogen or $C_1$-$C_4$-alkyl which may be substituted which at least one halogen; $R^5$ is NH—$R^6$; and $R^6$ is $C_1$-$C_4$-alkyl, $C_2$-$C_4$-alkenyl or $C_2$-$C_4$-alkynyl, wherein the alkyl, alkenyl and alkynyl groups may be substituted with at least one halogen or at least one cyano.

In still a further embodiment, $R^2$, $R^3$ and $R^4$ are each independently hydrogen, nitro, $C_1$-$C_4$-alkyl, $C_2$-$C_4$-alkenyl or $C_2$-$C_4$-alkynyl, wherein the alkyl, alkenyl and alkynyl groups may be substituted with at least one halogen or at least one cyano.

In still a further embodiment, $R^6$ is $C_1$-$C_4$-alkyl which may be substituted with at least one halogen or at least one cyano.

The compounds of formulas (II) may be used to prevent attack an crops by insects by treating the crop with a pesticidally effective amount of a compound of formula (II). Moreover, insects may be controlled by applying a pesticidally effective amount of the compound of formula (II) to the target insect or its locus. As such, the application may be carried out before or after the invention of the locus, growing crops, or harvested crops by insects.

A pesticidally effective amount of the compound/composition of the present invention will vary according to the prevailing conditions such as desired pesticidal effect and duration, weather, target species, locus, mode of application, and the like. In general, for use in treating crop plants, the rate of application of the compound and/or composition of this invention may be in the range of about 0.1 g to about 4000 g per hectare, desirably from about 25 g to about 600 g per hectare as the active ingredient, more desirably from about 50 g to about 500 g per hectare. For use in treating seeds, the typical rate of application is of from about 1 g to about 500 g per kilogram of seeds, desirably from about 2 g to about 300 g per kilogram of seeds, more desira-bly from about 10 g to about 200 g per kilogram of seeds. Customary application rates in the protection of materials are, for example, from about 0.001 g to about 2 kg, desirably from about 0.005 g to about 1 kg, of active compound per cubic meter of treated material.

The present compounds may be applied formulated or unformulated. Typical formulations contain the active ingredient in a range from about 0.1 ppm to about 10,000 ppm and may also contain a carrier. The carrier may be any agronomically acceptable carrier, including natural and synthetic organic and inorganic ingredients that facilitate dispersion of the composition or compound and contact with the pesticidal target. The carrier may be solid (e.g. clays, synthetic silicates, silica, resins, waxes, kaolin, bentonite, dolomite, calcium carbonate, talc, powdered magnesia, Fuller's earth, gypsum, diatomaceous earth, China clay, and combinations thereof); liquid (e.g. water, aqueous solutions, N-methylpyrrolidone, kerosene, cyclohexanone, methy-lethyl ketone, acetonitrile, methanol, ethanol, isopropyl alcohol, acetone, butyl cellosolved, 2-ethyl-1-hexanol, cyclohexanone, methyl cellulose, polyvinyl alcohol, sodium lignin sulfonates, polymeric alkyl naphthalene sulfonates, sodium naphthalene sulfonate, polymethylene bisnaphthalenesulfonate, sodium N-methyl-N-(long chain acid) laureates, hydrocarbons and other water-immiscible ethers, esters and keeonns, and combinations thereof); or a combination of solid and liquid carriers.

The compositions of the present invention may also contain one or more surface-active ingredients to increase the biological effectiveness of the active ingredient. Suitable surface-active ingredients include surfactants, emulsifying agents, and wetting agents. A wide range of surfactants is available and can be selected readily by those skilled in the art from "The Handbook of Industrial Surfactants", 2nd Edition; Gower (1997), which is incorporated herein by reference in its entirety for all purposes. There is no restriction an the type or chemical class of surfactant that can be used. Nonionic, anionic, cationic and amphoteric types, or combinations of more than one of these types, are all useful in particular situations.

Among nonionic surfactants, exemplary classes include polyoxyethylene alkyl, alkyne, alkynyl or alkylaryl ethers, such as polyoxyethylene primary or secondary alcohols, alkylphenols or acetylenic diols; polyoxyethylene alkyl or alkyne esters, such as ethoxylated fatty acids; sorbitan alkyl-esters, whether ethoxylated or not; glyceryl alkylesters; sucrose esters; and alkyl polyglycosides. Exemplary anionic surfactant classes include fatty acids, sulfates, sulfonates, and phosphate mono- and diesters of alcohols, alkylphenols, polyoxyethylene alcohols and polyoxyethylene alkylphenols, and carboxylates of polyoxy-ethylene alcohols and polyoxyethylene alkylphenols. These can be used in their acid form but are more typically used as salts, for example sodium, potassium or ammonium salts.

Cationic surfactants classes include polyoxyethylene tertiary alkylamines or alkenylamines, such as ethoxylated fatty amines, quaternary ammonium surfactants and polyoxyethylene alkylether-amines. Representative specific examples of such cationic surfactants include polyoxyethylene (5) cocoamine, polyoxy-ethylene (15) tallowamine, distearyldimethylammonium chloride, N-dodecylpyridine chloride and polyoxypropylene (8) ethoxytri-methylammonium chloride. Many cationic quatemary ammonium surfactants of diverse structures are known in the art to be useful in combination which active ingredients and can be used in compositions contemplated herein.

Suitable emulsifying agents and wetting agents include, but are not limited to, ionic and nonionic types such as polyacrylic acid salts, lignosulphonic acid salts, phenolsulphonic or naphthalene-sulphonic acids, products of polycondensation of ethylene oxide with fatty alcohols, fatty acids or fatty amines, substituted phenols (especially alkylphenols or arylphenols), sulphono-succinic acid ester salts, taurine derivatives (especially alkyl taurates), phosphoric esters of alcohols or products of poly-condensation of ethylene oxide with phenols, esters of fatty acids with polyhydric alcohols, and derivatives having sulphate, sulphonate and phosphate groups, of the componens above.

Compositions of this invention may also contain other active ingredients, for example other pes-ticides; insecticides; fertilizers such as ammonium nitrate; urea, potash, and superphosphate; phytotoxicants and plant growth regulators; safeners; and nematicides. These additional ingredients may be used sequentially or in combination with the above-described compositions. For example, the plant(s) may be sprayed with a composition of this invention either before or after being treated with other active ingredients. Such sequential applications may be performed by applying the combination of active ingredients individually within a one day period or less, such as separate applications of the individual pesticides within less than 1 hour, less than 5 hours, less than 10 hours, less than 14 hours, or less than 17 hours.

Other optional components may be admixed with the present compositions to facilitate the application and/or effectiveness of the active ingredient. To this end, optional components that may be added include antifoaming agents including silicone based antifoaming agents; thickening agents such as fumed silica; antimicrobial agents; antioxidants; buffers; dyes; perfumes; stabi-lizing agents; and antifreezing agents. Exemplary antifreezing agents include but are not limited to, glycols such as propylene glycol and ethylene glycol, N-methylpyrrolidone, cyclohexanone, and alcohols such as ethanol and methanol.

Compositions of the present invention may be present in any effective formulation, including, but not limited to, a dusting powder or granule; dispersible powder, granule or grain; aqueous dispersion; suspension; paste; or emulsion. As such, the composition may be applied by any effective method including, but not limited to, spraying, atomizing, dusting, spreading or pouring.

Powders, including dusting powders or granules and dispersible powders, granules or grains contain at least one active ingredient and an inert solid extender or carrier, such as kaolin, ben-tonite, dolomite, calcium carbonate, talc, powdered magnesia, Fuller's earth, gypsum, diatoma-ceous earth and China clay. Dispersible powders, granules and grains typically also include one or more wetting and dispersing agents, such as surfactants.

The composition of this invention may be made up of granules comprising 0.5 to 40%, preferably 2 to 30% by weight of the active compound of this invention as active ingredient; 1 to 20%, pref-erably 2 to 10% by weight of the surfactant; and 40 to 98.5%, preferably 20 to 96% by weight of solid carrier. Formulated into a dust, the composition may include 0.5 to 40%, preferably 1 to 35% by weight of the active ingredient; and 99.5 to 60%, preferably 99 to 65% by weight of finely divided solid carrier.

The composition of this invention may also be formulated into a paste comprising 0.1 to 20%, preferably 1 to 10% by weight of the active ingredient, 1 to 20%, preferably 2 to 10% by weight of surfactant; and 60 to 98.9%, preferably 80 to 97% by weight of paste base. In a wettable powder formulation, the composition typically includes 5 to 95%, preferably 10 to 50% by weight of the new compounds of this invention as active ingredient; 1 to 20%, preferably 5 to 10% by weight of surfactant; and 4 to 44%, preferably 40 to 85% by weight of solid carrier, the solid carrier being preferably ammonium sulfate.

The aqueous dispersions or emulsions may be prepared by dissolving the active ingredient in an organic solvent optionally containing wetting, dispersing or emulsifying agent(s) and then adding the mixture to water which may also contain wetting, dispersing or emulsifying agent(s). Suitable organic solvents are kerosene, cyclohexanone, methylethyl ketone, acetone, methanol, acetonitrile, and the like. The compositions may also be in the form of liquid preparations for use as dips or sprays which are generally aqueous dispersions or emulsions containing the active ingredient in the presence of one or more wetting agent(s), dispersing agent(s), emulsifying agent(s) or suspensiog agent(s).

Typical liquid solutions.include the active ingredient, a carrier, and optionally, a surface active agent. The dilute solutions of the present compositions generally contain about 0.1 to about 50 parts active ingredient, about 0.25 to about 50 parts carrier, and about 0 to about 94 parts surface active agent, all parts being by weight based an the total weight of the composition. Similarly, the concentrated compositions typically include about 40 to about 95 parts active ingredient, about 5 to about 25 parts carrier, and about 0 to about 20 parts surface active agent.

Emulsifications are usually solutions pesticides in water-immiscible or partially water-immiscible solvents as the carrier together with at least one surface active agent. Suitable solvents for the active ingredients of this invention include, but are not limited to, hydrocarbons and water-immiscible ethers, esters or ketones. The emulsification compositions generally contain from 5 to 95%, preferably 20 to 70% by weight of the active compound of this invention as active ingredient; 1 to 40%, preferably 5 to 20% by weight of surfactant; and 4 to 94%, preferably 10 to 75% by weight of liquid carrier.

The compounds useful in the present invention may be readily synthesized using techniques generally known by synthesic organic chemists, such as those described by R. V. Hoffman in "Organic Syntheses", Coll. Vol. 7, p. 508-511, describing m-trifluoro-methylbenzenesulfonyl chloride preparation, which is incorporated herein by reference in its entirety for all purposes. Exemplary synthesis methods are shown in the experimental section.

The present compositions may be prepared in a known manner, for example by homogeneously mixing or grinding the active ingredient(s) with other ingredients. Additional components may be admixed with the composition at any point during the process, including during and/or after any mixing step of the components.

Experimental:

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventions regard as their invention. Efforts have been made to ensure accuracy with respect to numbers (e.g., amounts, temperature, etc.) but some errors and deviations should be accounted for. Unless indicated otherwise, percent is percent by weight given the component and the total weight of the composition, temperature is in ° C. or is at ambient temperature, and pressure is at or near atmospheric.

Preparation of
4-Trifluoromethyl-pyridine-3-sulfonyl chloride

4-Trifluoromethyl-pyridine-3-sulfonyl chloride was prepared as shown in Scheme (I).

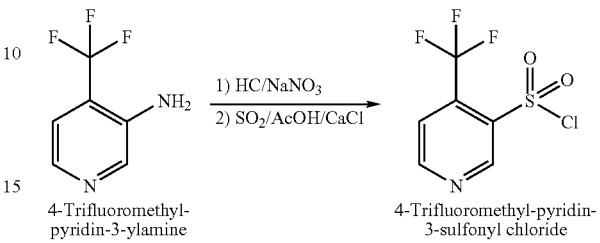

4-Trifluoromethyl-pyridin-3-ylamine

4-Trifluoromethyl-pyridin-3-sulfonyl chloride

4-Tifluoromethyl-pyridin-3-ylamine (2.27 g) in acetic acid (2 ml) was added to a solution of 37% HCl (4.7 ml) and acetic acid (2 ml) to obtain a homogeneous solution. The solution was cooled to (−5)° C. and sodium nitrite (0.97 g) in water (2 ml) was added dropwise, keeping the exothermic reaction at or below 0° C. When the addition was completed, the reaction temperature was maintained between (−5)° C. and (−10)° C. for 30 minutes to give a yellow slurry.

In a separate reaction vessel, sulfur dioxide gas was bubbled through 50 ml of acetic acid until it was saturated. Copper(II)chloride dihydrate (1.0 g) was added portionwise while stirring and bubbling in more sulfur dioxide. Copper (I)chloride (0.2 g) was added and stirring and bubbling of sulfur dioxide was continued for 20 minutes. This mixture was cooled to 5° C. and the yellow slurry described above was added portion-wise over 10 minutes. The reaction temperature was allowed to rise to ambient temperature over 1 hour while a gas was being evolved. It was then poured into water and ice and extracted three times with ether. The ether portions were combined, washed repeatedly with saturated sodium bicarbonate and then dried with magnesium sulfate. The drying agent was filtered away and the ether evaporated to yield 0.95 g of the 4-trifluoromethyl-pyridine-3-sulfonyl chloride, which was confirmed with LC/ms showing sulfonic acid at the solvent front of 10.52 min giving a MW of 227.

Preparation of
4-Trifluoromethyl-pyridine-3-sulfonic acid
prop-2-ynylamide (compound 1)

4-Trifluoromethyl-pyridine-3-sulfonic acid prop-2-ynylamide was prepared as shown in Scheme (II).

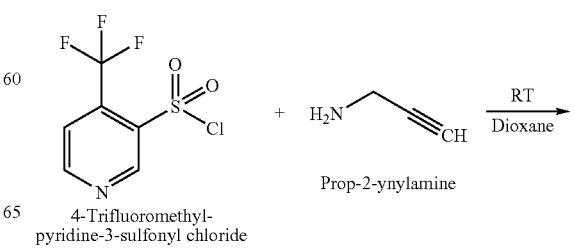

4-Trifluoromethyl-pyridine-3-sulfonyl chloride

Prop-2-ynylamine

-continued

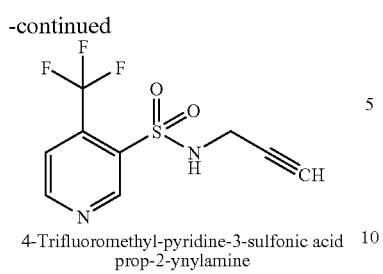

4-Trifluoromethyl-pyridine-3-sulfonic acid prop-2-ynylamine

4-Trifluoromethyl-pyridine-3-sulfonyl chloride (0.45 g) was dissolved in dioxane (3 ml), and pro-pargylamine (0.63 ml) was added to the mixture and allowed to stand at ambient temperature overnight. The reaction was diluted with 0.5% HCl and 37% HCl was added drop-wise until the mixture became acidic. This was extracted three times with-ethyl acetate. The ethyl acetate portions were combined, washed with saturated sodium bicarbonate and dried with magnesium sulfate. The drying agent was filtered away and the solvent evaporated to give 0.13 g of crude 4-trifluoromethyl-pyridine-3-sulfonic acid prop-2-ynylamide, which was chromatographed an silica gel using ethyl acetate and methylene chloride to yield 0.08 g of purified 4-Trifluoromethyl-pyridine-3-sulfonic acid prop-2-ynylamide. LC/ms analysis with RT=1.36 min yielded a purity of 98% m+/m− of 264.8/262.9. Melting-point of the purified compound tested as 97-98° C.

Preparation of
4-Trifluoromethyl-pyridine-3-sulfonic acid
cyanomethyl-amide (compound 2)

4-Trifluoromethyl-pyridine-3-sulfonic acid cyanomethyl-amide was prepared as shown in Scheme (III).

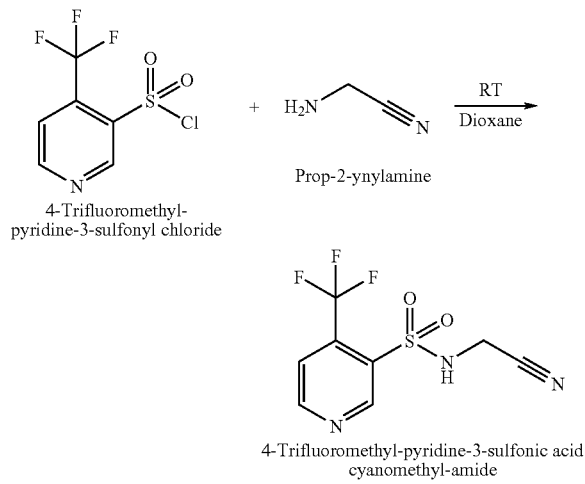

4-Trifluoromethyl-pyridine-3-sulfonyl chloride (0.45 g) was dissolved in dioxane (3 ml), and ami-noacetonitrile (1.0 g) was added to the mixture and allowed to stand at ambient temperature overnight. The reaction was diluted with 0.5% HCl and 37% HCl was added dropwise until the mixture became acidic. This was extracted three times with ethyl acetate. The ethyl acetate portions were combined, washed with saturated sodium bicarbonate and dried with magnesium sulfate. The drying agent was filtered away and the solvent evaporated to give 0.14 g of crude 4-Tri-fluoromethyl-pyridine-3-sulfonic acid cyanomethyl-amide, which was chromatographed an silica gel using methylene chloride to yield 0.06 g of purified 4-Trifluoromethyl-pyridine-3-sulfonic acid cyanomethyl-amide. LC/ms analysis with RT=1.12 min yielded a purity of 99% m+/m− of 265.87/263.88. Melting point of the purified compound tested as 158-159° C.

EXAMPLE 1

Insecticidal Evaluation of Test Compounds

Test compounds were prepared and formulated into aqueous formulations using acetone. The formulations were tested using the following target species:

SAW-L52-*PRODER* (southern armyworm), 2ND-3RD Instar Larvae, Leaf Dip, 4 days

CA-H43-*APHIGO* (cotton aphid), Mixed Life Stages, Leaf Dip

BA-H40-*APHIFA* (black bean aphid), Mixed Life Stages, Plant Drench

GPA-H52-*MYZUPE* (green peach aphid), Mixed Life Stages, Leaf Dip

SLWF-H45-*BEMIAR* (silver leaf whitefly), Adult, Leaf Dip

TSMR-A42-*TETRUR* (two-spotted spider mite, P-resistant origin), Mixed Life Soges, Leaf Dip The following procedures were used to obtain the results shown in Table 1b. Table 1a describes the rating scale.

Test Procedures for Southern armyworm (*Spodoptera eridania*) (SAW—foliar):

Selected 7-day-old greenhouse-grown Lima bean in 2 in. pots containing two plants with 2.5-3 in. long leaves. Prepared test solutions as needed in 50:50 acetone:water and 100 ppm Kinetics® surfactant.

Dipped leaves into test solutions to provide complete coverage of the leaf surfaces. Kept treated plants in the fume hood to dry. Used one pot/treatment.

Placed pots with treated plants into a perforated clear plastic bag and arranged bags in ascend-ing order of treatment numbers an a 3×5 grid of plant holdings trays. Introduced ten $2^{nd}$-instar southern armyworm larvae into each bag and closed the bag. Placed the trays with bags in the holding room at 25±2° C., 20-40% relative humidity and continuous light for 4 days.

The bags were perforated twice using a custom-built device for puncturing 8-10 bags with 180 holds/bag (1 mm diam.) to provide 360 aeration holds in the bag. The larvae were added into the bags using tweezers or an insect aspirator.

Counted the number of surviving larvae and converted counts to mortality ratings using the values provided in Table 1a.

Treatments are assessed without opening the bags if at least six healthy appearing larvae (comparable to check larvae) are visible. If less than six larvae were visible, or if the larvae differed in appearance from the check larvae, the bag was emptied into a dissecting tray for counting and/or determining morbidity.

Moribund larvae were considered dead. Morbidity was defined as the inability to revert to the ventral position (including delayed reverting compared to check larvae).

Test Procedures for Cotton aphid (*Aphis gossypii*) (CA—leaf dip):

Selected cotton plants to the cotyledon stage (one plant per pot). Placed one heavily infested cotyledon pair, hosting approximately 100 laboratory-reared aphids, an top of each test plant. Allowed the aphids to transfer to the test plants (overnight). Removed the drying cotyledons from the test plants prior to dipping.

Prepared test solutions as needed in 50:50 acetone: water and 100 ppm Kinetic® surfactant. Dipped the infested leaves of the intact plant into the test solution to provide complete coverage of the leaf surfaces. Placed in a well-vented area to dry.

Estimated the aphid survival, relative to the average number of aphids and converted to a mortality rating as shown in Table 1a.

Test Procedures for Bean aphid (*Aphis fabae*) (BA—Foliar):

Transferred approximately 5-day-old nasturtium seedlings (at the state of unfolded cotyledons), grown in Metro mix in propagation trays in the greenhouse, to Rootcubes, which were held in propagation trays Pressed the seed (still attached to the seedling) in the central depression of each cube. Held transferred seedlings for approximately 3 days in the greenhouse for expansion of the cotyledons.

In the insecticide screening laboratory, infested the seedlings. Positioned a paint roller screen above the 72 plants in each tray so that the screen was in contact with the foliage of the test plants. Spread approximately 50 infested nasturtium stems and leaves (from approximately 2-3 peat pots of insectary-reared aphids) an each screen. Kept the trag with the seedlings sitting in about ½ in. water overnight in the laboratory (leaving lights in lab on). Migration of aphids to the test plants occurred by morning. Removed the screen with drying leaves from the trays of test plants and discarded the leaves.

Prepared test solutions as needed in 50:50 acetone:water and 100 ppm Kinetic® surfactant. Selected plants to dip that had approximately 2-30 aphids per plant. Dipped each plant into the test solution to provide complete coverage of the foliage, stem, protruding seed surface and surrounding cube surface. Kept treated plants in the fume hood to dry. For routine screening, used one plant/treatment.

Placed treated plants in bioassay trays, 1 plant/well. Added water to fill each well. This allowed the plants to be watered from the roots, not interfering with the foliar treatment, and reduced potential migration of aphids between treatments. Kept treated plants at room temperature an the insecticide screening lab bench with continuous fluorescent light for 3 days.

Visually estimated, as a percentage, the reduction of live population verses the check using the scale provided in Table 1a.

Test Procedures for GPA—Green peach aphid (*Myzus persicae*)—Leaf Dip:

Selected pepper plants (one plant per pot) in the second leaf-pair stage, with the 1$^{st}$ leaf-pair measuring 6-10 cm from tip to tip. Removed the cotyledons. Placed infested pepper leaves or leaf sections on top of the test plants, allowing for approximately 60 laboratory-reared aphids per plant. Allowed the aphids to transfer from the leaf sections to the test plants (overnight) to reach a density of at least 40 aphids per plant, then removed the leaf sections.

Prepared test solutions as needed in 50:50 acetone:water and 100 ppm Kinetic® surfactant (STP#1A). Dipped the leaves of the infested plant into the test solution to provide complete coverage of the leaf surfaces. Placed in a well-vented area to dry. Test plants were maintained under fluorescent light (24 hour photoperiod) at 25±2° C. and 20-40% relative humidity for five days, at which time aphid survival was determined (see Table 1a).

Test Procedures for Silverleaf Whitefly (*Bemisia arzentifolii*)(SLWF):

Selected cotton plants grown to the cotyledon state (one plant per pot). Prepared test solutions as needed in 50:50 acetone:water and 100 pm Kinetic0 surfactant. Dipped the cotyledons of the intact plant into the test solution to provide complete coverage of the foliage. Placed in a well-vented area to dry.

Placed each pot with treated seedling in a 16-oz clear plastic cup (TP 16 Solo(D) and introduced 10 to 12 whitefly adults (approximately 3-5 day old adults). The insects are collected using an aspirator operated by the house vacuum system and ¼-inch, non-toxic Tygon@ tubing (R-3603) connected to a barrier pipette tip. Adjusted the suction of the vacuum by touching the tip to your skin until the suction just begins to pull at the skin. The tip, containing the collected insects, was then gently inserted into the soil containing the treated plant, allowing insects to crawl out of the tip to reach the foliage for feeding. The cups were covered with a re-usable screened lid (1.5×1.5 inch of 150 micron mesh polyester screen PeCap from Tetko Inc).

Maintained test plants in the holding room at 25±2° C. and 20-40% relative humidity for three days avoiding direct exposure to the fluorescent light (24 hour photoperiod) to prevent trapping of heat inside the cup. Assessed the survival of the whiteflies in 3 days after treatment of the plants (see Table 1a for rating scale).

Test Procedures for Two-spotted spider mite (*Tetranychus uriticae*) TSM—leaf-dip:

Selected lima bean plants (one plant per pot), grown to the first leaf pair with a span of 7-12 cm. Placed sections of a heavily infested leaf (laboratory reared mites) an the test plants. Allowed the mites to transfer from the leaf sections to the test plants (at least two houss) to provide at least 100 mites per leaf. Removed the leaf sections from the test plants prior to dipping.

Prepared test solutions as needed in 50:50 acetone:water and 100 ppm Kinetic® surfactant. Dipped the infested leaves of the intact plant into the test solution to provide complete coverage of the leaf surfaces. Placed in a well-vented area to dry.

Maintained test plants in the holding room under fluorescent light (24 hour photoperiod) at 25±2° C. and 20-40% relative humidity for five days.

Estimated the percentage of dead mites (nymphs and adults) relative to the total population an the treated leaves and converted to the mortality rating of Table 1a.

TABLE 1a

Mortality Rating for assays targeting Worms and Whitefly

| # Surviving larvae of 10 | 0-9 mortality rating | (% mortality) |
|---|---|---|
| 0 | 9 | (100) |
| 1 | 8 | (90) |
| 2 | 7 | (80) |
| 3 | 6 | (70) |
| 4 | 4 | (60) |
| 5 | 3 | (50) |
| ≧6 | 0 | (≦40) |

Observations
R = Reduced feeding, regardless of cause (e.g., repellent effects)
Rating Scales
Activity Rating for assays targeting Aphids and Mites
9 = 100% reduction of live population vs. check
8 = 86-99% reduction of live population vs. check
7 = 75-85% reduction of live population vs. check
5 = 50-74% reduction of live population vs. check
3 = 25-49% reduction of live population vs. check
0 = 0-25% reduction of live population vs. check TABLE 1b Example 1 Experimental Results

| Test Compound No. | Dose | Units | SAW L52 | CA H43 | BA H40 | GPA H52 | SLWF H45 | TSMR A42 |
|---|---|---|---|---|---|---|---|---|
| 1 | 300 | ppm | 0 | 8 |   | 8 |   | 0 |
| 1 | 300 | ppm |   | 8 | 8R | 8 | 0 |   |
| 1 | 100 | ppm |   | 8 | 5R | 7 | 0 |   |
| 1 | 10  | ppm |   | 0 | 0  | 0 | 0 |   |
| 2 | 300 | ppm | 0 | 9 |   | 8 |   | 0 |
| 2 | 300 | ppm |   | 9 | 7R | 5 |   |   |
| 2 | 100 | ppm |   | 8 | 0R | 3 |   |   |
| 2 | 10  | ppm |   | 0 | 0  | 0 |   |   |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein it is intended that the specification and examples be considered as exemplary only, with a true scope and Spirit of the invention being indicated by the following claims.

The invention claimed is:

1. A pyridine-3-sulfonyl compound having the formula (I)

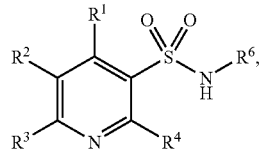

wherein
R$^1$ is trifluoromethyl;
R$^2$, R$^3$ and R$^4$ are each independently hydrogen, nitro, C$_1$-C$_4$-alkyl, C$_2$-C$_4$-alkenyl, C$_2$-C$_4$-alkynyl or phenyl, wherein the alkyl, alkenyl, alkynyl and phenyl groups may be substituted with at least one halogen or at least one cyano;
R$^5$ is halogen or NHR$^6$;
R$^6$ is C$_1$-C$_4$-alkyl, C$_2$-C$_4$-alkenyl, C$_2$-C$_4$-alkynyl or phenyl, wherein the alkyl, alkenyl, alkynyl and phenyl groups may be substituted with at least one halogen or at least one cyano;
or an isomer, salt or ester thereof.

2. The pyridine-3-sulfonyl compound of claim 1, wherein R$^5$ is halogen.

3. The pyridine-3-sulfonyl compound of claim 1, wherein R$^5$ is NHR$^6$.

4. The pyridine-3-sulfonyl compound of claim 1, wherein the compound is 4-trifluoromethyl-pyridine-3-sulfonyl chloride.

5. The pyridine-3-sulfonyl compound of claim 1, wherein R$^2$, R$^3$ and R$^4$ are each independently hydrogen or C$_1$-C$_6$-alkyl which may be substituted with at least one halogen; R$^5$ is NHR$^6$; and R$^6$ is C$_1$-C$_6$-alkyl, C$_2$-C$_6$-alkenyl, or C$_2$-C$_6$-alkynyl, wherein the alkyl, alkenyl and alkynyl groups may be substituted with at least one halogen or at least one cyano.

6. The pyridine-3-sulfonyl compound of claim 1, wherein the compound is 4-trifluoromethyl-pyridine-3-sulfonic acid prop-2-ynylamide, 4-trifluoromethyl-pyridine-3-sulfonic acid cyanomethylamide or a mixture thereof.

7. An insecticidal composition comprising
a) at least one compound of the formula (II)

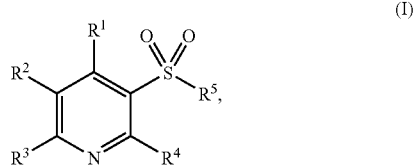

wherein
R$^1$ is trifluoromethyl;
R$^2$, R$^3$ and R$^4$ are each independently hydrogen, nitro, C$_1$-C$_4$-alkyl, C$_2$-C$_4$-alkenyl, C$_2$-C$_4$-alkynyl or phenyl, wherein the alkyl, alkenyl, alkynyl and phenyl groups may be substituted with at least one halogen or at least one cyano;
R$^6$ is C$_1$-C$_4$-alkyl, C$_2$-C$_4$-alkenyl, C$_2$-C$_4$-alkynyl or phenyl, wherein the alkyl, alkenyl, alkynyl and phenyl groups may be substituted with at least one halogen or at least one cyano;
or an isomer or salt thereof, and
b) an agronomically acceptable carrier.

8. The composition of claim 7, wherein R$^2$, R$^3$ and R$^4$ are each independently hydrogen or C$_1$-C$_6$-alkyl which may be substituted with at least one halogen; and R$^6$ is C$_1$-C$_6$-alkyl, C$_2$-C$_6$-alkenyl or C$_2$-C$_6$-alkynyl, wherein the alkyl, alkenyl and alkynyl groups may be substituted with at least one halogen or at least one cyano.

9. The composition of claim 7, wherein the compound is 4-trifluoromethyl-pyridine-3-sulfonic acid prop-2-ynylamide, 4-trifluoromethyl-pyridine-3-sulfonic acid cyanomethylamide or a mixture thereof.

10. The composition of claim 7, wherein the composition is formulated into a dusting powder or granule, a dispersible powder, granule or grain, an aqueous dispersion, a suspension, a paste or an emulsion.

11. The composition of claim 7, wherein the composition is applied at a rate of about 50 g per hectare to about 500 g per hectare.

12. A method for controlling insects comprising contacting an insect or their food supply, habitat or breeding grounds with a pesticidally effective amount of at least one compound of the formula (II)

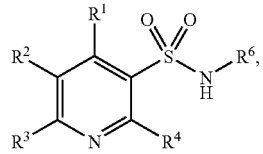

where in
R$^1$ is trifluoromethyl;
R$^2$, R$^3$ and R$^4$ are each independently hydrogen, nitro, C$_1$-C$_4$-alkyl, C$_2$-C$_4$-alkenyl, C$_2$C$_4$-alkynyl or phenyl, wherein the alkyl, alkenyl, alkynyl and phenyl groups may be substituted with at least one halogen or at least one cyano;

$R^6$ is $C_1$-$C_4$-alkyl, $C_2$-$C_4$-alkenyl, $C_2$-$C_4$-alkynyl, or aryl, wherein the alkyl, alkenyl, alkynyl, and aryl groups may be substituted with at least one halogen or at least one cyano;

or an isomer or salt thereof.

13. The method of claim 12, wherein the compound is applied at a rate of about 50 g per hectare to about 500 g per hectare.

14. The method of claim 12, wherein the compound is applied as part of a composition that further comprises an agronomically acceptable carrier.

15. A method for protecting growing plants from attack or infestation by insects comprising contacting a plant, or soil or water in which the plant is growing, with a pesticidally effective amount of a compound of the formula (II) as defined in claim 7.

16. The method of claim 15, wherein the compound is applied at a rate of about 50 g per hectare to about 500 g per hectare.

17. The method of claim 15, wherein the compound is applied as part of a composition that further comprises an agronomically acceptable carrier.

* * * * *

UNITED STATES PATENT AND TRADEMARK OFFICE
CERTIFICATE OF CORRECTION

| | | |
|---|---|---|
| PATENT NO. | : 7,365,042 B2 | Page 1 of 1 |
| APPLICATION NO. | : 10/495929 | |
| DATED | : April 29, 2008 | |
| INVENTOR(S) | : Haley et al. | |

It is certified that error appears in the above-identified patent and that said Letters Patent is hereby corrected as shown below:

On the Title of the patent:

In subsection (86): "PCT/EP02/31368" should read --PCT/EP02/13168--

A subsection (60) should be added as follows:
        --Related U.S. Application Data
        (60)   Provisional application No. 60/332,059, filed November 23, 2001.--

Item (57); in the abstract, second line after formula (I): "directed lo" should read --directed to--

In the claims:

In Claim 12, col. 14, indicated line 61: "where in" should read --wherein--

In Claim 12, col. 14, indicated line 64: "$C_2C_4$-alkynyl" should read --$C_2$-$C_4$-alkynyl--

Signed and Sealed this

Fifteenth Day of July, 2008

JON W. DUDAS
*Director of the United States Patent and Trademark Office*